United States Patent [19]
Hammen et al.

[11] Patent Number: 6,013,808
[45] Date of Patent: Jan. 11, 2000

[54] METHOD OF PURIFYING CARBAZOLE ESTER PRECURSORS OF 6-CHLORO-α-METHYL-CARBAZOLE-2-ACETIC ACID

[75] Inventors: Philip D. Hammen, East Haddam; Peter R. Rose, Ledyard; John L. Tucker, Niantic; Keith M. Devries, Chester; Diane M. Rescek, Oakdale, all of Conn.

[73] Assignee: Pfizer Inc., New York, N.Y.

[21] Appl. No.: 09/292,138

[22] Filed: Apr. 15, 1999

Related U.S. Application Data

[60] Provisional application No. 60/089,480, Jun. 16, 1998.
[51] Int. Cl.[7] .................... C07D 209/82; C07D 209/84
[52] U.S. Cl. ............................................. 548/444
[58] Field of Search ............................................. 548/444

[56] References Cited

U.S. PATENT DOCUMENTS

| | | | |
|---|---|---|---|
| 4,193,923 | 3/1980 | Gurien et al. | 260/315 |
| 4,264,500 | 4/1981 | Zwamlen | 260/315 |

OTHER PUBLICATIONS

Reymond et al., Heterocycles (1982), 19(12), 2345–7, 1982.
Ross et al., J. Pharm. Sci. (1984), 73(9), 1211–15, 1984.

*Primary Examiner*—Laura L. Stockton
*Attorney, Agent, or Firm*—Peter C. Richardson; Paul H. Ginsburg; Raymond M. Speer

[57] ABSTRACT

A process of purifying a (6-chloro-2-carbazolyl)methyl-malonic acid di($C_1$–$C_6$ alkyl) ester of Formula (I):

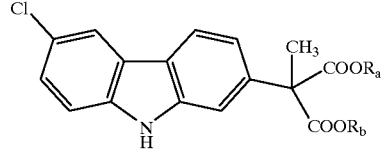

(I)

wherein $R_a$ and $R_b$ must be the same and are selected from the group consisting of $C_1$–$C_6$ alkyl; comprises phase separating one or more impurities from said carbazole ester at least once wherein the solvent used to carry out said phase separation is acetic acid. In a preferred embodiment said acetic acid is glacial acetic acid which is maintained at a temperature of from about 30° to about 110°0 C. and said carbazole ester is obtained in a purity of at least 99.90% by weight, so that the amount of impurities present therein is 0.10% or less by weight. In a more preferred embodiment of said process, said temperature is from about 50° to about 70° C., and said phase separation is carried out only once.

10 Claims, No Drawings

METHOD OF PURIFYING CARBAZOLE ESTER PRECURSORS OF 6-CHLORO-α-METHYL-CARBAZOLE-2-ACETIC ACID

REFERENCE TO RELATED APPLICATIONS

The present application is based on Provisional Application Ser. No. 60/089,480 filed on Jun. 16, 1996, now abandoned, the benefit of the filing date of which is hereby claimed.

BACKGROUND OF THE INVENTION

The present invention is in the field of methods of purifying organic compounds, including but not limited to those organic compounds which are the final products and intermediates, especially the latter, produced by synthetic methods in organic chemistry. In particular, the methods are for purifying alkyl esters of organic compounds which are carboxylic acids. The present invention relates to an improved method of purifying by phase separation (6-chloro-2-carbazolyl)methyl-malonic acid di($C_1$–$C_4$ alkyl) esters, especially the diethyl ester, which is sometimes referred to hereafter as the "carbazole ester", although this term is also used as a general reference to all of the di($C_1$–$C_4$ alkyl) esters involved in the method of the present invention.

The carbazole ester is the starting material for one process of making carprofen, a highly effective COX-2 selective anti-inflammatory drug approved by the Food and Drug Administration, Committee on Veterinary Medicine (FDA/CVM) for use in dogs in the United States. The carbazole ester starting material is known to potentially contain at least one impurity, created during one step of a related manufacturing process, which may comprise as much as 0.9% by weight of the carbazole ester starting material. The composition of this impurity is discussed in detail further below, but the purification method of the present invention is contemplated to include within its scope not only this impurity but other impurities as well. In order to obtain carprofen final product in sufficiently pure form for use as an animal drug, all such impurities must be reduced to a minimum.

BRIEF DESCRIPTION OF THE STATE OF THE ART

Zwahlen U.S. Pat. No. 4,264,500 discloses a method for making 6-chloro-α-methyl-carbazole-2-acetic acid. The final intermediate for the final product is (6-chloro-2-carbazolyl)methyl-malonic acid diethyl ester, which in accordance with the description in Zwahlen is converted thereto by hydrolysis and decarboxylation. The conversion steps are said to be alternatively carried out in situ or following isolation of said penultimate intermediate in a known manner, for example, by crystallization. However, there is no suggestion in Zwahlen of the method of purifying such an intermediate as that provided by the present invention, or of the surprisingly high yields produced in accordance with the method of the present invention.

SUMMARY OF THE INVENTION

In accordance with the broadest aspects of the present invention there is provided a method of purifying a (6-chloro-2-carbazolyl)methyl-malonic acid di($C_1$–$C_4$ alkyl) ester of Formula (I):

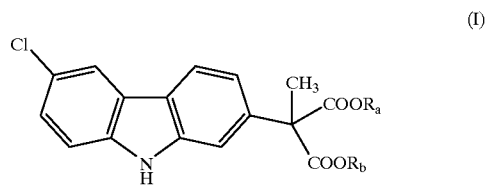

wherein $R_a$ and $R_b$ must be the same and are selected from the group consisting of $C_1$–$C_4$ alkyl; comprising phase separating one or more impurities from said ester at least once wherein the solvent used to carry out said phase separation is acetic acid.

In accordance with the present invention there is further provided the above-described method of purifying said ester of Formula (I) wherein said ester is obtained at a purity of at least 99.80% by weight, so that the amount of impurities present therein is 0.20% or less by weight; and still further wherein said acetic acid is glacial acetic acid, maintained at a temperature of from about 30° to about 110° C.; and further wherein said phase separation is optionally carried out two or more times.

Still further, there is provided in accordance with the present invention the above-described method of purifying said ester of Formula (I) wherein said ester is the diethyl ester; and further still wherein said ester of Formula (I) is obtained in a purity of at least 99.90% by weight, so that the amount of impurities present therein is 0.10% or less by weight; and further wherein said acetic acid is glacial acetic acid which is maintained preferably at a temperature of from about 40° to about 90° C., more preferably from about 45° to about 75° C., and most preferably from about 50° to about 70° C.; and further wherein said phase separation is carried out only once.

In accordance with narrower, but no less preferred embodiments of the present invention, said (6-chloro-2-carbazolyl)methyl-malonic acid di($C_1$–$C_6$ alkyl) ester of Formula (I) which is to be purified is present in the form of a dispersed solid, whether amorphous or crystalline, which forms predominantly a slurry in the glacial acetic acid solution thereof.

Further, it is provided that said impurities may be produced directly or indirectly in the course of a method of preparation of said ester and may comprise any one or more of starting materials, synthesis intermediates, reactants, reaction side products, degradation products, solvents in which various reaction steps of said method of preparation have been carried out, or undesired analogs of closely related chemical structure to said ester of Formula (I). It is particularly provided that said impurities may arise indirectly from said method of preparation as the result of said method being carried out improperly or on a suboptimal basis.

It is also provided that said impurities may be derived inadvertently from sources which do not include being directly or indirectly produced during said method of preparation of said ester of Formula (I), e.g., from contamination of the equipment in which said method of preparation is carried out, from contamination of the starting materials, solvents or synthesis aids used in said method of preparation, from contaminants in the encompassing atmosphere, i.e., the environment surrounding said method of preparation which become absorbed into said method, or from contamination of said ester of Formula (I) while being stored or handled subsequent to preparation thereof.

In a particularly preferred embodiment of the purification method of the present invention, the intermediate to be purified is the carbazole (diethyl) ester and the impurity to be removed is a dimer of Formula (IV):

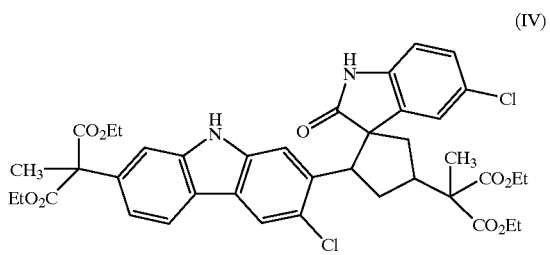

(IV)

DETAILED DESCRIPTION OF THE INVENTION

The above-described (6-chloro-2-carbazolyl)methyl-malonic acid di($C_1$–$C_6$ alkyl) ester of Formula (I):

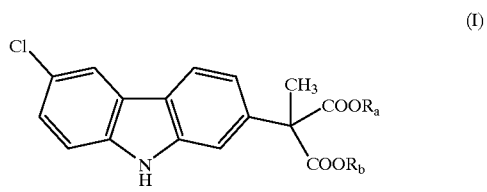

(I)

wherein $R_a$ and $R_b$ must be the same and are selected from the group consisting of $C_1$–$C_4$ alkyl, which is to be purified in accordance with the methods of the present invention, is the final intermediate in the synthesis of carprofen. Carprofen, as already described, is an approved anti-inflammatory drug especially useful in the treatment of pain and inflammation in dogs.

It is required that $R_a$ and $R_b$ be the same and that they be selected from the group consisting of $C_1$–$C_4$ alkyl. If $R_a$ and $R_b$ were allowed to represent different alkyl groups, for example methyl and ethyl, thereby resulting in mixed diesters, then the malonic acid carbon would become a chiral center, giving (S) and (R) enantiomers of the ester of Formula (I). This result would further complicate and probably wholly defeat satisfactory purification of the ester precursor of Formula (I). For example, it would then be necessary to utilize known methods for phase separation of the diastereoisomers formed from the racemic mixture by combination with an optically pure molecule, e.g., tartaric acid and its derivatives.

$R_a$ and $R_b$ are used herein as different substituent identifiers despite the fact that the moieties which they represent must both be the same. The purpose of this differing identification is to emphasize that potential impurities from which the ester of Formula (I) must be separated include mixed esters that may be produced by the improper running of a method of preparation or by some other, unknown or unforeseen occurrence. $R_a$ and $R_b$ are selected from $C_1$–$C_4$ alkyl which may be straight chain or branched, and include methyl, ethyl, n-propyl, iso-propyl, n-butyl, sec-butyl, and tert-butyl. Of these representative species, methyl and ethyl, and particularly ethyl, are preferred.

Carprofen, 6-chloro-α-methyl-9H-carbazole-2-acetic acid, which is prepared from the ester precursor of Formula (I), may be represented by Formula (II):

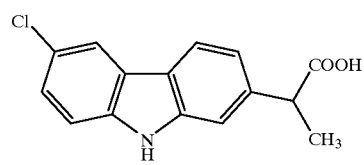

(II)

It will be noted that the active agent carprofen of Formula (II) differs from the ester precursor of Formula (I) with regard to having been hydrolyzed and mono-decarboxylated. In a preferred method of manufacturing carprofen, the carbazole ester precursor of Formula (I) has its own intermediate, shown further below in Formula (III). The carbazole ester precursor of Formula (I), in turn, differs from the intermediate of Formula (III) which precedes it by having been aromatized by the introduction of two additional double bonds into the phenyl ring to which the α-methyl-acetic acid moiety is attached. This will be readily appreciated from the depiction of the intermediate of Formula (III) as follows:

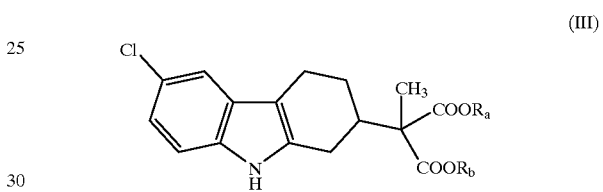

(III)

The above-mentioned modifications of the carbazole ester precursor of Formula (I) and its preceding intermediate of Formula (III) take place in a preferred method of manufacturing carprofen which is carried out in accordance with the synthesis steps described in the above-mentioned Zwahlen U.S. Pat. No. 4,264,500.

The first step in the Zwahlen synthesis is to aromatize the intermediate of Formula (III) by treating it with chlorine. This step is preferably carried out in an aprotic solvent such as toluene, methylene chloride or ethylene chloride at an elevated temperature such as the reflux temperature of the reaction mixture, while chlorine is slowly added to said mixture. The addition of the chlorine preferably takes place over a 2 to 8 hour period of time. In a typical manner of carrying out this step, toluene is used as the solvent and the reaction is carried out at 75° C. for 4 hours. The aromatized compound which results is the carbazole ester precursor represented by Formula (I):

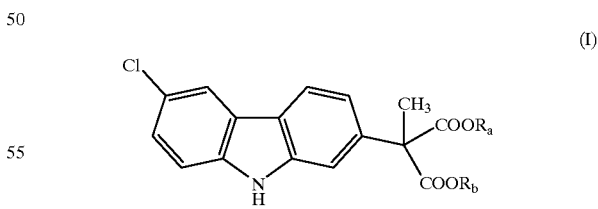

(I)

Aromatization of the ester of Formula (III) produces the carbazole ester intermediate represented by Formula (I) above, which is then subjected to hydrolysis and decarboxylation in order to produce the carprofen final product. In a preferred manner of carrying out this last-mentioned synthesis step, the intermediate of Formula (I) is hydrolyzed and decarboxylated in accordance with known methods involving treatment with acids, e.g., a combination of glacial acetic acid and hydrochloric acid.

The above-described synthetic transformations may be represented together in accordance with the following reaction scheme:

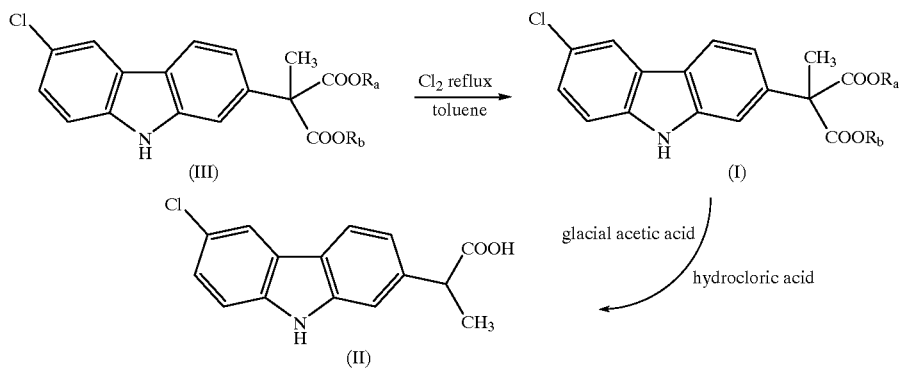

It is broadly contemplated in accordance with the present invention that the impurity or impurities which are separated from the ester precursor of Formula (I) may vary significantly in character and may originate from different sources. Inherently, the purification which is carried out in the present invention relies on the basic nature of purification processes generally, which as a preferred embodiment, is a phase separation procedure. Such known processes can achieve very high levels of separation, even of compounds that are very closely related in structure, as is explained in more detail further below. The parameters of the purification process of the present invention have been chosen in such a way that said process will not owe its operability and superior selectivity to the structure of the impurities which are being separated. It is not contemplated, therefore, that the present invention is limited in any way by the character of such impurities.

An investigation has been undertaken of one of the more troublesome impurities encountered with respect to the carbazole ester precursor of Formula (I). This impurity appears over time as a precipitate in solutions of said ester precursor, as well as in solutions of the carprofen final product of Formula (II). The impurity has been identified by X-ray crystallography and other analytical data as a spiro oxindole dimer form of the carbazole ester precursor which is produced during the aromatization step involving chlorination of the intermediate of Formula (III) as above-depicted in the synthesis scheme. The structure of the spiro oxindole dimer impurity may be represent by Formula (IV):

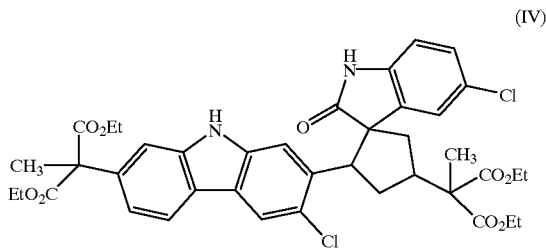

The dimer impurity possesses crystallization properties which pose a challenge to conventional purification procedures, which may be negated by coprecipitation. Initial attempts to achieve the required levels of purification produced by the purification method of the present invention using conventional solvent systems were not successful. Acetone, acetonitrile, ethanol, propanol, butanol, ethyl acetate, N,N-dimethylformamide, N,N-dimethylacetamide, methyl isobutyl ketone, and combinations of these solvent systems resulted in increased dimer impurity levels due to the above-mentioned kinetic crystallization effects of these solvent systems. More acceptable results were achieved using toluene/methanesulfonic acid, and toluene/butanol solvent systems. The yields (75–85%) and product quality (<0.1% dimer impurity) obtained with the toluene/methanesulfonic acid system were satisfactory, while the yields from the toluene/butanol system were lower. The toluene/methanesulfonic acid system was then carried out under stress conditions intended to simulate those which would be encountered during actual manufacturing. The purification was carried out at elevated temperatures of 60–65° C. for extended times of >2 hrs. These stress conditions produced a degradation product which could not be isolated and removed.

Satisfactory results were also obtained initially with an ethanol/isopropyl ether recrystallization which gave high yield and good removal of impurities. When this purification system was subjected to stress experiments using extended granulation times, however, the production results were unacceptable. The crystallization was kinetic in nature with the product crystallizing out first followed by the dimer impurity within 1 hr. This time interval within which the dimer impurity also crystallized out is too short for production on a commercial scale.

The solvent system which was successful, and on which the present invention is based, was that involving warm acetic acid. The warm acetic acid system repulp, i.e., phase separation slurry, held up under stress experiments which consisted of extended granulation time (>36 hrs.), extended heating time (>12 hrs.), and excessive heating (>70° C.). The acetic acid solvent system was subsequently scaled up for production of 40 kg quantities, which involved changes in cycle times as well as in equipment. The production run was highly successful, producing only 0.02% of dimer impurity, determined by HPLC assay.

In addition to the particular above-mentioned spiro oxindole dimer impurity, many other potential impurities clearly exist. These impurities may be produced directly or indirectly in the course of a method of preparation of said carbazole ester precursor of Formula (I) and may comprise any one or more of starting materials, synthesis intermediates, reactants, reaction side products, degradation products, solvents in which various reaction steps of said method of preparation have been carried out, or undesired analogs of closely related chemical structure to said carbazole ester of Formula (I). Said impurities most typically would arise during the ordinary procedures involved in the particular method of preparation which was being employed, and are therefore referred to herein as being related "directly" to said method of preparation.

However, it is frequently the case that a method of preparation is improperly designed as to its basic chemical engineering, utilizing inadequate starting materials, reactants or solvents or requiring inappropriate process parameters such as the time and temperature for carrying out the reaction. On the other hand, a method of preparation may be based on perfectly appropriate chemical engineering, but in the course of its execution some inadvertent mistake is made. For example, the wrong starting material or an improper quantity of reactant may be used; or the temperature at which the reaction is carried out may be too high or too low. Such errors of execution can also produce impurities along with the desired final product. Impurities of these types arise outside the scope of the procedures involved in the method of preparation being employed, and are therefore referred to herein as being related "indirectly" to said method of preparation.

It is also possible that impurities may not be related either directly or indirectly to a method of preparation. Instead such impurities may be derived inadvertently from different sources, e.g., from contamination of the equipment in which the method of preparation is carried out, from contamination of the starting materials, solvents or synthesis aids used in the method of preparation, from contaminants in the encompassing atmosphere, i.e., the environment surrounding the method of preparation. Impurities from these sources may become absorbed into the procedures of the preparation method. After the preparation method is completed, it is necessary to separate the final product and then handle it or store it in some fashion preparative to its formulation into a pharmaceutical composition in accordance with known procedures. Thus, impurities can arise as the result of contamination of said ester of Formula (I) while it is being stored or handled subsequent to preparation thereof, by contact with the source of said impurities.

The purification process of the present invention provides for a yield of the carbazole ester precursor of Formula (I) sufficiently high that the purity of said carbazole ester precursor final product is at least 99.80% by weight, so that the weight of impurities therein is 0.20% or less by weight. The indicated percentage by weight is based on the weight of ester precursor in the final product divided by the weight of said final product×100. It is frequently more convenient, however, to calculate the percentage purity from the results of a quantitative analysis of the final product which determines the amount of impurity present, from which the percentage purity is then calculated. Such quantitative analytical procedures are well known, any one or more of which may be adapted to the needs of the process herein described.

In a preferred embodiment of the present invention, said carbazole ester precursor of Formula (I) is the diethyl ester and said carbazole ester precursor is obtained in a purity of at least 99.90% by weight, so that the amount of impurities present therein is 0.10% or less by weight. In a still more preferred embodiment of the present invention, said carbazole ester precursor of Formula (I) is the diethyl ester and said carbazole ester precursor is obtained in a purity of at least 99.95% by weight, so that the amount of impurities present therein is 0.05% or less by weight.

The acetic acid which is employed may be in the form of a highly concentrated non-aqueous solution, in which the acetic acid is the significantly predominant component. However, such non-aqueous solutions of acetic acid will usually be associated with lower levels of purity in the carbazole ester precursor of Formula (I) final product. Accordingly, in preferred embodiments of the present invention said acetic acid is glacial acetic acid.

The purification process of the present invention in a preferred embodiment thereof uses hot acetic acid as the solvent, which is applied to a solid product comprising the carbazole ester precursor of Formula (I) and the impurities contained therein. The impurities to be removed are highly soluble in this hot acetic acid solvent, but the final product carbazole ester precursor has a very low solubility in the hot acetic acid solvent. The insolubility level of the carbazole ester precursor of Formula (I) in the hot acetic acid solvent is on the order of about 85% by weight, i.e., only about 15% of the carbazole ester precursor will be dissolved in the hot acetic acid. The remaining carbazole ester precursor is present as a solid which is dispersed in the hot acetic acid solvent and may therefore be accurately described as a slurry or pulp. After as much of the carbazole ester precursor has been precipitated from the hot acetic acid solvent as possible, it and the already dispersed carbazole ester precursor which has not dissolved in the solvent are separated from the solvent. This separation constitutes a phase separation in which the solid phase carbazole ester precursor is separated from the liquid phase in which the impurities are dissolved.

The acetic acid solvent is maintained at a temperature of from about 30° to about 110° C.; preferably at a temperature of from about 35° to about 90° C., more preferably from about 40° to about 75° C., and most preferably from about 45° to about 70° C. The precipitation process, i.e., the phase separation process which includes the bulk of the carbazole ester precursor in slurry form, may be carried out as many times as desired. While each round of phase separation will yield a more pure product, this will be achieved at the cost of additional expended energy, and therefore of reduced efficiency. However, it is one of the surprising advantages of the present invention that purity as high as at least 99.90% by weight, and as high as 99.95% by weight or higher, including even 99.98% by weight can be achieved from a single phase separation. Carrying out the phase separation process twice is usually all that is required to obtain a final product of the high purity required for commercial distribution as an animal health drug.

It is further contemplated that the purification process of the present invention may be carried out in a number of different embodiments with respect to the character and process history of the carbazole ester precursor of Formula (I) which is to be purified. For example, it contemplated that said carbazole ester precursor material may be in the form of a solid isolated as an intermediate from a process of preparation such as that above-described in more detail. Said carbazole ester precursor material may have been isolated as a solid in order to permit its storage for later processing at the same manufacturing site, or its transport for finishing at a different manufacturing facility. Such an isolated solid intermediate represents an excellent opportunity to conveniently remove impurities which are present, since the processing of the carbazole ester precursor in accordance with the present invention will be fully compatible with the manufacturing synthesis sequence of steps which are being utilized. Said isolated solid carbazole ester precursor intermediate may be treated directly with the hot acetic acid phase separation solvent of the process of the present invention. In a less preferred embodiment, said solid intermediate carbazole ester precursor may first be dissolved in some non-aqueous solvent which is compatible with the acetic acid to be subsequently added.

The purification process of the present invention is to be carried out not only in accordance with the disclosure herein, but also in accordance with principles of purification procedures, especially phase separation procedures, which are well known in the art. These principles are briefly described hereinbelow in order to summarize those considerations which would most frequently play a role in modifications of the purification process of the present invention by the artisan skilled in this art. The summary of these principles also serves to highlight the unpredictable nature of the results of phase separation processes generally, and of the unexpected success of the process of the present invention in particular.

Thus, e.g., purification by phase separation in accordance with the present invention involves not only the presence of the ester precursor in dispersed, slurry form, but some precipitation of the ester precursor as well, which must take place while the impurities are maintained in a dissolved state in the acetic acid solvent. Precipitation is usually regarded as consisting essentially of the process of separating solid particles from a previously clear solution by physical or chemical changes therein. This is to be distinguished, then, from the presence of the ester precursor in a dispersed state from the outset of the purification process of the present invention. One of the most important uses of phase separation is in the purification of solids, where it may be referred to in general as precipitation.

In its most simple aspect, phase separation involves an impure solid which is dissolved in a suitable solvent at elevated temperatures, and upon cooling, the bulk of the impurities remain solubilized while the precipitated product is separated therefrom and thereby purified. In the case of the ester precursors of Formula (I) the product has a low solubility even in the presence of the acetic acid solvent at high temperatures, resulting in the initial formation of a slurry. The phase separation process of the present invention may be repeated several times if desired, and the acetic acid solvent may be used at various temperatures.

The solid ester precursor of Formula (I) which is the product of the purification by phase separation process of the present invention may be amorphous or in the form of crystals, or in both forms. If amorphous in form, the solid final product may comprise any one of a number of different shapes and sizes, and these amorphous particles may also be agglomerated or flocculated together to form larger masses. If crystalline in form, the solid final product may comprise more than one crystalline form, and these may also appear in combination. The size of the crystalline particles may vary over a wide range of sizes.

In more specific terms, phase separation or crystallization refers to the production of a solid, single-component, amorphous or crystalline phase from a multicomponent fluid phase, and in the case of the present invention, said fluid phase is an acetic acid solution in which the undesired impurities are dissolved. Where the object of the phase separation or crystallization is to prepare a pure dry solid, which is the case with some of the embodiments of the present invention, it will be necessary to separate the solid from said fluid phase, and this is usually accomplished by centrifugation or filtration, followed by drying. The advantageous properties of such a dry solid amorphous or crystalline product include ease of handling, stability, good flow properties and an attractive appearance. Generally, phase separation or crystallization is carried out in jacketed or agitated vessels, and the conditions necessary to obtain suitable purity, yield and possibly crystal form, must be determined by experimentation.

Where the phase separation involves dispersed crystal particles or crystallization from solution, it will take place in three basic stages: induction of supersaturation, formation of nuclei and crystal growth. At a given temperature and concentration, a solution may be saturated by either cooling or by removing solvent. It is also possible to add a third component which reduces the solubility of the solute, or to carry out a chemical reaction in a solvent in which the resulting product has a low solubility. With further cooling or concentration, the supersaturated metastable region is entered. Low levels of supersaturation are unlikely to produce spontaneous formation of crystal nuclei, but crystal growth can be initiated by adding seeds. At lower temperatures or higher concentrations which fall on the curve limiting the metastable region, spontaneous nucleation is virtually certain and crystal growth occurs under these conditions as well.

When the boundary of the metastable region is exceeded, the rate of nucleation rapidly increases, and the crystallization process becomes uncontrolled. Consequently, it is desirable to maintain the state of the solution within the metastable region. The width of the area under the curve of the metastable zone is affected most importantly by the agitation, the cooling rate, the presence of soluble additives, the solvent, and the thermal history of the particular solution.

Nucleation entails the formation of small nuclei around which crystals grow. Thus, without nucleation, crystal growth cannot occur. When a material crystallizes from a solution, nucleation and crystal growth occur simultaneously over a wide intermediate temperature range. Nucleation is dependent on the degree of supercooling, with low degrees of supercooling resulting in little or no nucleation. However, the rate of nucleation rises to a maximum and then falls, so that excessive cooling may depress the rate of crystallization by limiting the number of nuclei formed. Spontaneous nucleation occurs when sufficient molecules of low kinetic energy come together in a context where their mutual attraction is sufficient to overcome their individual momentum. Once a certain size is reached, the nucleus becomes stable in the prevailing conditions, and as the temperature drops, more low energy molecules are present and the rate of nucleation rises. These circumstances partially characterize the formation of the above-theorized dimer impurity which is especially troublesome in solutions of the ester precursor of Formula (I) as above-described.

The formation of crystal nuclei or nucleation is also a process which determines the size of the product crystals and further, plays a substantial role in determining a number of the physical properties of said crystals, and more importantly in the present case, their purity.

Regarding crystal growth, at higher temperatures the molecules are too energized to remain captive in the crystal lattice, while at lower temperatures, more molecules are retained and the growth rate increases. Ultimately, however, diffusion to and orientation at the crystal surface becomes depressed at still lower temperatures. Deposition on the faces of the crystal causes depletion of the molecules in the immediate vicinity. Thus, the driving force of crystal growth is provided by the concentration gradient framework, from supersaturation in the solution to lower concentrations at the crystal face. Accordingly, a high level of supersaturation promotes a high rate of crystal growth.

Correct positioning and suitable orientation with respect to the crystal lattice results in a loss of kinetic energy by the molecules involved. The aggregate, referred to as the heat of crystallization must be conducted away, i.e., transferred to some surface from the entire solution, and thus the rate of crystal growth is influenced by both the rate of heat transfer and the changes which are taking place at said surface. For example, it is well known that agitation of the system increases heat transfer by reducing the thermal resistance of the liquid layers adjacent to the crystal until the changes at the crystal face become the controlling effect. Initially, agitation quickly increases the growth rate by decreasing the thickness of this boundary layer and the diffusional resistance. However, as agitation is intensified, a limiting value is reached which is determined by the kinetics of the surface reaction.

The several stages through which growth units or precursors pass during crystal growth reveals additional critical factors, e.g., transport through the bulk solution to an impingement site not necessarily the growth cite of the crystal, adsorption at the impingement where precursors shed solvent molecules and solvent is transported back into the solution, diffusion of the precursors from the site of impingement to a growth site, and incorporation into the crystal lattice after desolvation during which it is also possible for solvent to be adsorbed before escaping into the solution. All of these processes depend on the morphology of the interfacial region.

Various models of crystal growth have been used in the art in order to identify the growth mechanisms of a crystal face and consequently the interfacial processes as well. For example, volume diffusion and surface diffusion models are used, as well as two dimensional nucleation and spiral growth models. Also, overall growth rates are measured in accordance with different methods in the art, but from the point of view of the theory of crystal growth, the linear growth rate of a crystal plane is most frequently used. Further, the measurement of nucleation rates and of nucleation kinetics is achieved through different approaches. One of these is the measurement of the induction period, which is the time that elapses between the achievement of supersaturation and the appearance of a solid phase in the system being studied. The induction period is considered to be inversely proportional to the rate of nucleation. In a crystallizer, both the nucleation and the crystal growth compete for the supersaturation, and both contribute to the final product size distribution.

In order to obtain crystals of high compositional uniformity, and therefore of high purity, it is important the linear growth rate be kept constant over the whole advancing interface, i.e., that the crystal shape remains unchanged during growth.

The soluble impurities from which the final product precipitate is separated by crystallization may either increase or reduce the nucleation rate. For example, insoluble materials may act as nuclei and thereby promote crystallization. Impurities may also affect crystal form. Due to the presence of these impurities, the composition of the solid precipitate differs from that of the coexisting fluid during crystallization. This phenomenon is referred to as segregation and it is important to crystal growth for a variety of reasons, the central question in each case being to what extent the crystal composition reflects that of the nutrient from which it grows.

Depending upon their contributions to the Gibbs free energy of the crystal, impurities are either partly rejected or preferentially taken up by the advancing interface. Thus, a segregation coefficient is defined based on the interfacial transfer of the impurity. Further, it is known that impurity-solvent interaction and complex formation leads to a complicated concentration dependence of the segregation coefficient. Segregation is also important with respect to crystal growth kinetics itself, since impurities can strongly influence the growth kinetics. When a crystal grows from an impure solution, it will generally reject the impurity if this is less soluble in the crystal than in the solution. As the interface moves, the impurity may be rejected into the solution more rapidly than it can be carried away by diffusion. Consequently, the impurity concentration in the solid will be determined by the impurity concentration in the enriched diffusion layer and not by the mean concentration in the solution. Accordingly, segregation performed in a controlled manner can be advantageously employed for purification of materials.

It is well known in the art that large differences in the maximum attainable supersaturation and nucleation rates of crystals can result from the proper choice of solvent-solute system. Further, there are significant differences in the maximum attainable supersaturation, $\Delta C_{max}$, when the solvent changes from polar to nonpolar, and there is the obvious correlation between $\Delta C_{max}$ and solubility. The higher the solubility, the lower the supersaturation at which nucleation occurs; thus, nucleation is easier when the solution is more concentrated. The choice of solvent also has a significant impact on crystal growth. The growth kinetics of crystals growing from solution are determined by two factors related to the nature of the growing interface: the degree of molecular roughness and the nature of the adsorption of the solvent on the surface.

When the desired parameters for the phase separation procedures are chosen in accordance with the above-discussed principles and as described herein, and then applied to the process of the present invention, the resulting specific embodiments of the purification process will then be carried out in suitable apparatus for obtaining the desired result. The purpose of the phase separation or crystallization process itself is to produce on an optimal basis amorphous or crystal particles of the required shape, size distribution, purity and yield. Where crystallization is involved, this is achieved by maintaining a degree of supersaturation at which nucleation and crystal growth proceed at appropriate rates. In addition to solubility of the solute and the temperature, other important factors include the thermal stability of the solute, the nature of the impurities present, and the degree of hydration required.

The ester precursor solute in the process of the present invention is largely insoluble in the hot acetic acid solvent from the outset of the process. However, the ester precursor which is dissolved at this stage will increase substantially with increased temperature, supersaturation and the deposition of a large proportion of the solute is usually brought about in a suitable crystallizer apparatus by cooling a hot concentrated solution. Thus, the mother liquors following evaporative crystallization can be cooled to yield a further crop of crystals. Alternatively, a crystallizer apparatus which employs flash evaporation might be used. In such an apparatus, a hot solution is passed into a vacuum chamber in which both evaporation and cooling take place. Optimally, the crystallizer which is utilized should produce crystals of even size, which facilitates the removal of the mother liquor and washing. If large quantities of the liquor are occluded in the mass of crystals, drying will yield an impure product unacceptable in terms of the present invention. A further advantage is that crystals of even size are less likely to cake on storage.

Batch production of large, uniform crystals can be achieved using agitated reaction vessels in which slowly controlled or wholly natural cooling takes place. As crystallization takes place, the degree of supersaturation and the concentration of the solute fall, ultimately reaching a saturation where growth ceases. Closer control of this process may be obtained by artificially seeding the supersaturated solution in the absence of natural nucleation. Continuous production of large, even crystals may be achieved using Oslo or Krystal crystallizers in which a metastable, supersaturated solution is released into the bottom of a mass of growing crystals on which the solute is deposited. The crystals are fluidized by the circulation of the solution and classification, i.e., stratification in this zone allows the withdrawal of sufficiently large crystals from the bottom of the crystallizer.

Crystallizers are usually classified by the way in which a solution is supersaturated, e.g., a cooling crystallizer or an evaporative crystallizer. A vacuum crystallizer entails both processes. Batch crystallization in a cooling crystallizer is carried out in closed tanks agitated by stirrers in which both the specific heat of the solution and the heat of crystallization are removed by means of jackets or coils through which recirculated cooling water is passed. Agitation is important for preventing temperature gradients in such tanks, opposing sedimentation and irregular crystal growth at the tank bottom, and for facilitating crystal growth.

Where it is desired to carry out the crystallization process on a continuous basis, the crystallizer apparatus may take the form of a trough cooled in the same manner as above-described with regard to tanks. The solution enters at one end and the crystals and liquid are discharged at the other end. Agitation in such an apparatus may be achieved using a slow moving worm which works in the solution and lifts crystals off of the cooling surface to distribute them through the solution and slowly convey them through the trough. Rocking of the entire trough can also be used in combination with baffles which increase the residence time of the solution in the trough. Both of these types of crystallizers are characterized by low heat transfer coefficients, and a more rapid heat exchange may be achieved by using a double-pipe arrangement in which the crystallizing fluid is carried in the central pipe with the countercurrent flow of the coolant in the annulus between the pipes. Agitation in this type of apparatus is often achieved by the use of a shaft which rotates in the central pipe and carries blades which scrape the heat transfer surface, permitting high heat transfer coefficients to be obtained.

Evaporative crystallizers can be simple pan-like arrangements or stirred reaction vessels. For larger production levels, calandria are employed for heating and the downcomer, which must be large enough to accommodate the flow of the suspension, commonly houses an impeller, with forced circulation increasing the heat transfer to the boiling liquid. A continuous process in which close control of the crystal product size is important may be carried out using an Oslo crystallizer, which saturates the solution by evaporation. In a vacuum crystallizer, typically a hot concentrated solution is fed to an agitated crystallization chamber maintained at low pressure. The solution boils and cools adiabatically to the boiling point corresponding to the operating pressure of the crystallizer. Crystallization follows concentration and the product is removed from the bottom of the vessel.

BRIEF DESCRIPTION OF A PREFERRED EMBODIMENT

Immediately below there is set out a working example of an embodiments of the present invention for the purpose of further illustrating the same, but without any intention of thereby limiting the scope of the present invention, to which the claims herein are directed.

EXAMPLE 1

Purification of Carbazole Ester Precursor

There was added to a reaction vessel 30.0 g of a specific production lot of carbazole ester precursor, (6-chloro-2-carbazolyl)methyl-malonic acid diethyl ester, previously determined to have 0.6% by weight of a spiro oxindole dimer impurity having the following structure:

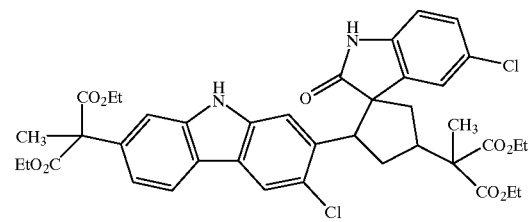

The carbazole ester precursor material was combined with 90 mL of glacial acetic acid and heated to 50–55° C. with stirring. A thin slurry developed which was stirred for approximately 2.5 hrs. at that temperature. The slurry was then slowly cooled to 20–25° C., stirred for an additional 2 hrs., and then filtered and dried. The yield of carbazole ester final product obtained was 23.14 g (77%), which contained 0.028% by weight of the spiro oxindole dimer impurity.

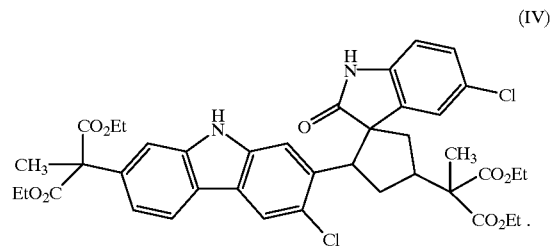

What is claimed is:

1. A process of purifying a (6-chloro-2-carbazolyl) methyl-malonic acid di($C_1$–$C_6$ alkyl) ester of Formula (I):

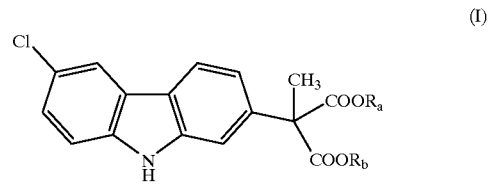

(I)

wherein $R_a$ and $R_b$ must be the same and are selected from the group consisting of $C_1$–$C_6$ alkyl;

comprising phase separating one or more impurities from said carbazole ester at least once wherein the solvent used to carry out said phase separation is acetic acid.

2. A process in accordance with claim 1 wherein said acetic acid is glacial acetic acid which is maintained at a temperature of from about 30° to about 110° C.

3. A process in accordance with claim 2 wherein said temperature is from about 50° to about 70° C., and said phase separation is carried out only once.

4. A process in accordance with claim 1 wherein said carbazole ester of Formula (I) is the diethyl ester.

5. A process in accordance with claim 4 wherein said carbazole ester is obtained in a purity of at least 99.95% by weight, so that the amount of impurities present therein is 0.05% or less by weight.

6. A process in accordance with claim 5 wherein said carbazole ester of Formula (I) which is to be purified is present in the form of an isolated crystalline solid.

7. A process in accordance with claim 1 wherein said one or more impurities are produced directly or indirectly in the course of a process of preparation of said ester and comprise one or more of starting materials, synthesis intermediates, reactants, reaction side products, degradation products, solvents in which various reaction steps of said process of preparation have been carried out.

8. A process in accordance with claim 7 wherein said one or more impurities arise indirectly from said process of preparation as the result of said method being carried out improperly or on a suboptimal basis.

9. A process in accordance with claim 1 wherein said one or more impurities are derived inadvertently from contamination of equipment in which a process of preparation of said carbazole ester of Formula (I) is carried out, from contamination of starting materials, solvents or synthesis aids used in said process of preparation, from contaminants in the environment surrounding said process of preparation which become absorbed into said process, or from contamination of said carbazole ester of Formula (I) while being stored or handled subsequent to preparation thereof by said process of preparation.

10. A process in accordance with claim 1 wherein said one or more impurities comprises a spiro oxindole dimer of Formula (IV):